(12) United States Patent
Dahlmann et al.

(10) Patent No.: US 10,301,212 B2
(45) Date of Patent: May 28, 2019

(54) RADIOPAQUE GLASS AND USES THEREOF

(71) Applicant: SCHOTT AG, Mainz (DE)

(72) Inventors: Ulf Dahlmann, Landshut (DE); Sabine Pichler-Wilhelm, Landshut (DE); Jens Suffner, Landshut (DE)

(73) Assignee: SCHOTT AG, Mainz (DE)

( * ) Notice: Subject to any disclaimer, the term of this patent is extended or adjusted under 35 U.S.C. 154(b) by 0 days.

(21) Appl. No.: 15/658,814

(22) Filed: Jul. 25, 2017

(65) Prior Publication Data

US 2018/0029925 A1 Feb. 1, 2018

(30) Foreign Application Priority Data

Jul. 29, 2016 (DE) .......................... 10 2016 114 109

(51) Int. Cl.
| | | |
|---|---|---|
| A61K 6/083 | (2006.01) | |
| C08L 33/04 | (2006.01) | |
| C03C 3/083 | (2006.01) | |
| C03C 3/089 | (2006.01) | |
| C03C 4/08 | (2006.01) | |
| C03C 3/118 | (2006.01) | |
| C03C 3/064 | (2006.01) | |
| A61K 6/00 | (2006.01) | |
| C03C 4/00 | (2006.01) | |

(52) U.S. Cl.
CPC .............. *C03C 4/087* (2013.01); *A61K 6/002* (2013.01); *A61K 6/0005* (2013.01); *A61K 6/0091* (2013.01); *C03C 3/064* (2013.01); *C03C 3/118* (2013.01); *C03C 4/0021* (2013.01)

(58) Field of Classification Search
USPC ......................................................... 523/117
See application file for complete search history.

(56) References Cited

U.S. PATENT DOCUMENTS

| | | |
|---|---|---|
| 5,641,347 A | 6/1997 | Grabowski et al. |
| 6,297,181 B1 | 10/2001 | Kunert et al. |
| 6,342,302 B1 * | 1/2002 | Steidl .................... C03C 4/0021 106/35 |
| 7,895,164 B1 | 2/2011 | Varadarajan et al. |
| 8,268,065 B2 | 9/2012 | Ritter et al. |
| 2008/0255265 A1 | 10/2008 | Hoescheler et al. |
| 2009/0298966 A1 | 12/2009 | Vanini et al. |

FOREIGN PATENT DOCUMENTS

| | | |
|---|---|---|
| DE | 41 00 604 | 2/1992 |
| DE | 4443173 | 7/1996 |
| DE | 19849388 | 5/2000 |
| DE | 19945517 | 8/2000 |
| DE | 102 22 964 | 11/2003 |
| DE | 102005051387 | 1/2007 |
| DE | 102009008951 | 10/2010 |
| DE | 102011084501 | 3/2013 |
| EP | 0885606 | 12/1998 |
| EP | 1 547 572 | 6/2005 |
| GB | 2 251 814 | 7/1992 |
| GB | 2495587 | 4/2013 |
| JP | 2004-2062 | 1/2004 |
| WO | WO 2005/060921 | 7/2005 |
| WO | WO 2007/034258 | 3/2007 |
| WO | WO 2012/080513 | * 6/2012 |

OTHER PUBLICATIONS

DIN 12116 Testing the Resistance of Glass to Attack by Boiling Hydrochloric Acid Solution, and Classification, Mar. 2001, 5 Pages (in English).
DIN EN ISO 4049 Dentistry—Polymer-Based Restorative Materials, Mar. 2010, 34 Pages (in Enlgish).
International Standard ISOS 695 Glass-Resistance to Attack by a Boiling Aqueous Solution of Mixed Alkali-Method of Test and Classification,Third Edition, May 15, 1991, 5 Pages (In English).
International Standard ISO 719 Glass—Hydrolytic Resistance of Glass Grains at 98° C.—Method of Test and Classification, Second Edition, Oct. 1, 1985, 5 Pages (in English).

* cited by examiner

*Primary Examiner* — Tae H Yoon
(74) *Attorney, Agent, or Firm* — Collard & Roe, P.C.

(57) ABSTRACT

The amorphous, or at least partially crystalline, glass-based joining material is suitable for high-temperature applications, particularly in fuel cells and/or sensors. In addition to $SiO_2$ and $B_2O_3$ as glass formers, the joining material similarly contains BaO and CaO, whereby the amount of $Al_2O_3$ is limited. The joining material has a coefficient of linear thermal expansion of at least $7.0 \cdot 10^{-6}$ $K^{-1}$ in a range of 20° C. to 300° C. The joining material can be used for joining ferritic high-grade steels and/or chromium-containing alloys and/or ceramics, such as stabilized zirconium oxide and/or aluminium oxide.

26 Claims, 2 Drawing Sheets

RADIOPAQUE GLASS AND USES THEREOF

CROSS-REFERENCE

The invention described and claimed herein below is also described in German Patent Application 10 2016 114 109.7, filed Jul. 29, 2016, in Germany. The aforesaid German Patent Application, whose subject matter is incorporated herein by reference thereto, provides the basis for a claim of priority of invention for the invention claimed herein below under 35 U.S.C. § 119 (a)-(d).

BACKGROUND OF THE INVENTION

1. The Field of the Invention

The invention relates to a lead-free radiopaque glass and to uses thereof.

2. Description of the Related Art

In the dental sector, polymer-based dental compositions are increasingly being used for dental restoration. These polymer-based dental compositions consist customarily of a matrix of organic resins and various inorganic fillers. The inorganic fillers consist predominantly of powders of glasses, (glass-)ceramics, quartz or other crystalline substances (e.g. $YbF_3$), sol-gel materials and/or Aerosils, and are added as filler to the polymer-based composition.

The aim of using polymer-based dental compositions is to prevent possible harmful side-effects of amalgam and also to enhance aesthetics. Depending on the polymer-based dental compositions selected, they may be used for a variety of dental restoration measures, as for example for dental fillings or inlays, onlays, etc., and also for crowns and bridges.

The filler as such is intended on curing to minimize the shrinkage resulting from the polymerization of the resin matrix, and at the same time to increase the abrasion resistance. Where, for example, there is strong adhesion between tooth wall and filling, excessive polymerization shrinkage may result in fracture of the tooth wall. If the adhesion is not sufficient for this purpose, excessive polymerization shrinkage may bring about the formation of marginal gaps between tooth wall and filling, which may promote secondary caries.

Furthermore, certain physical and chemical requirements are imposed on the fillers:

It must be possible for the filler to be processed to give very fine powders. The finer the powder, the more homogeneous is the appearance of the filling. At the same time there is an improvement in the polishability of the filling, leading to improved abrasion resistance, via the reduction in the surface area open to attack, and so to a filling which retains its durability for longer. So that the powders are easy to process, moreover, it is desirable if the powders do not suffer agglomeration.

It is advantageous, if the filler is coated with a functionalized silane, since this facilitates the formulation of the dental composition and improves the mechanical properties. The surfaces of the filler particles are customarily covered at least partly with the functionalized silane.

In terms of its transparency and, where appropriate, index of refraction, the dental glass filler should conform as close as possible to the resin matrix. Furthermore, in its entirety, which thus also includes the filler, the polymer-based dental composition is adapted aesthetically to the natural tooth material, to make it as indistinguishable as possible from the surrounding, healthy tooth material. A very small particle size of the powdered filler likewise plays a part with regard to this aesthetic criterion.

Effective chemical resistance of the fillers, especially with regard to water, may make a contribution, furthermore, to a long lifetime of the dental restoration measures.

It is absolutely vital for the treatment of patients, furthermore, that dental restoration measures are visible in an X-ray image. Since the resin matrix is generally invisible in the X-ray image, the fillers have to ensure the necessary X-ray absorption. A filler of this kind which provides adequate absorption of X-rays is referred to as being radiopaque. Responsible in general for the radiopacity are constituents of the filler, examples being certain components of a glass, or additives. Such additives are also called radiopacifiers. A customary radiopacifier, besides dental glass fillers, is $YbF_3$, which may be added in crystalline, ground form.

According to DIN ISO 4049, the radiopacity of dental glasses or dental materials is reported, relative to the X-ray absorption of aluminium, as the aluminium equivalent thickness (ALET). A relative ALET is based on a sample thickness of 2 mm. The relative ALET of 200%, therefore, means that a glass plate having plane-parallel surfaces with a thickness of 2 mm produces the same attenuation of X-rays as an aluminium plate with a thickness of 4 mm. Analogously, a relative ALET of 500% means that a glass plate having plane-parallel surfaces of 2 mm in thickness produces the same attenuation of X-rays as an aluminium plate 10 mm thick. Below, the radiopacity of the glasses is reported by statements of the relative ALET (in %).

Because the polymer-based dental composition in the application is customarily introduced from cartridges into cavities, where it is modelled, it is intended frequently to be thixotropic in the uncured state. This means that its viscosity decreases when pressure is exerted, whereas without exposure to pressure it is dimensionally stable.

With regard to the filling materials, the inert compositions are distinguished from the reactive dental compositions. The reactive dental compositions include the dental cements. In the case of dental cements, examples being glass ionomer cements, the chemical reaction of the fillers with the organic acid leads to the curing of the dental composition, meaning that the curing properties of the dental composition and thus its workability are influenced by the reactivity of the fillers. The process involved here is often one of setting, which may be preceded by a superficial radical curing, under the action of UV light, for example. The glass here may serve as a filler, which triggers or participates in the chemical reaction, or else as an inert additive which is not involved in the reaction. In that case the chemical reaction is determined by further fillers likewise present in the glass ionomer cement.

Aside from the pure inert fillers and the pure reactive fillers, there are various intermediate stages, which cannot be listed here in detail. As examples of the intermediate stages, mention may be made of "compomers" and "resin modified glass ionomer cement" (RMGIC).

Composites, also called filling composites, in contrast, contain further fillers which in chemical terms are largely inert, since their curing characteristics are determined by constituents of the resin matrix, being therefore determined initially, and a chemical reaction of the fillers and/or additives is often undesired here.

Since on the basis of their different compositions glasses represent a class of material having diverse properties, they are frequently employed as fillers for polymer-based dental compositions. Applications other than as dental material, either in pure form or as a component of a materials mixture, are also possible, as for example for inlays, onlays, facing material for crowns and bridges, material for artificial teeth or other material for prosthetic, preservative and/or preventive tooth treatment. In their application as dental material, such glasses are referred to generally as dental glasses.

Another desirable property of the dental glass, in addition to those described above, is freedom from lead oxide (PbO), which is toxic.

Dental glasses therefore represent particularly high-grade glasses. Such glasses may likewise be employed in optical applications, especially where the application profits from the radiopacity of the glass. Because the radiopacity means that the glass absorbs electromagnetic radiation in the region of the X-ray spectrum, such glasses are at the same time filters for X-radiation. Sensitive electronic components may be damaged by X-radiation. In the case of electronic image sensors, for example, the passage of an X-ray quantum may damage the corresponding region of the sensor or may lead to an unwanted sensor signal which can be perceived, for example, as image interference and/or noisy pixels. For certain applications therefore it is necessary, or at least advantageous, for the electronic components to be protected from X-radiation, by filtering out such radiation from the spectrum of the incident radiation, using corresponding glasses.

Numerous dental glasses and other optical glasses having similar optical position or comparable chemical composition are described in the prior art, but these glasses exhibit considerable disadvantages in production and/or in use. In particular, many of the glasses contain sizeable proportions of fluorides and/or $Li_2O$, which evaporate very readily during melting and fusing, thereby complicating the precise establishment of the glass's composition.

Chemically inert, barium-free dental glasses for use as a filler in composites are subject matter of DE 198 49 388 A1. In the case of the low-index glasses, the glasses proposed therein necessarily include proportions of ZnO and F. The latter proportions may lead to reactions with the resin matrix, which may in turn have consequences for its polymerization behaviour. Moreover, the $SiO_2$ proportion, at 20-45 wt %, is limited to allow the glass described to include sufficient radiopacifier and F. In particular, in the case of low ZnO and $ZrO_2$ contents, the addition of up to 27 wt % of SrO is recommended.

WO2005/060921 A1 describes a glass filler, which is to be suitable particularly for dental composites. It contains 9 to 20 mol % of alkali metal oxides. The objective in that specification is to provide glass particles whose concentration of alkali metal ions is lower at the edge of the particles than in their centre. This means that the glasses described have a deliberate chemical instability, since otherwise it would not be possible to attain this concentration behaviour. It can be assumed that the necessarily low chemical stability is achieved by the stated proportions of the alkali metals in the original glass.

An alkali metal silicate glass serving as a filler for dental material is described in EP 0885606 B1. In the glass, which is of high $SiO_2$ content, the $Al_2O_3$ proportion of at least 5 wt % raises the viscosity and so leads to very high melting temperatures. Sodium oxides and potassium oxides are included as mandatory components. Moreover, the glass contains no components giving it radiopacity.

DE 4443173 A1 comprises a barium-free glass of high zirconium content, having a $ZrO_2$ content of more than 12 wt %, and other oxides. Such fillers are too reactive, especially for modern dental compositions based, for example, on acrylate, with which excessively rapid, uncontrolled curing can occur. Zirconium oxide in this quantity has a tendency towards devitrification. It produces phase separation, possibly with nucleation and subsequent crystallization. Moreover, such glasses can only be produced with high alkali metal contents, in order to ensure not too high a melting temperature, which would overstrain the melting assemblies. In turn, however, such high contents of alkali metal are deleterious to the chemical stability of the glasses.

DE 199 45 517 A1 likewise describes a glass of high zirconium content which, in applications in the dental sector, displays the same problems as the glasses in the aforementioned specification.

DE 10 2005 051 387 B3 describes as dental glass a magnesium aluminosilicate glass which in order to achieve radiopacity and an index of refraction of 1.50 to 1.549, has high contents of $La_2O_3$ and/or $Y_2O_3$ and also $WO_3$ and $ZrO_2$. This glass is free from barium, strontium and alkali metal oxides. In view of the high magnesium oxide content of such glasses, they tend towards phase separation. Another disadvantage is the high crystallization susceptibility, owing to the contents of $WO_3$ and $ZrO_2$. These contents additionally raise the melting temperatures. $La_2O_3$ is a very costly raw material and ought therefore to be avoided.

DE 10 2009 008 951 A1 discloses a radiopaque, barium-free glass and the use thereof as dental glass, mandatorily containing zirconium oxide. In order to achieve a narrow index of refraction range of 1.518 to 1.533, $ZrO_2$ is used with $Cs_2O$ and/or $La_2O_3$. In order that such glasses can be melted, furthermore, a high $K_2O$ proportion is required. Here again, a problem with such glasses is the crystallization tendency in combination with the relatively high melting temperatures and the raw materials costs occasioned by the $La_2O_3$ used. Glasses with low indices of refraction are not described by this prior art.

DE 10 2011 084 501 B3 discloses a barium-free, radiopaque glass having an index of refraction of 1.50 to 1.58. The glass is based on a combination of SrO and $La_2O_3$ and $ZrO_2$ as radiopacifier. Furthermore, $Cs_2O$ may be added to increase the radiopacity. Disadvantages of these glasses are the high melting temperatures and the crystallization tendency. $La_2O_3$, as described above, is very expensive.

JP 2004-002062 A discloses a glass substrate for flat screens. Besides SrO, the glasses disclosed contain primarily BaO and also high proportions of $Al_2O_3$ and MgO. The $Al_2O_3$, SrO, BaO and MgO components are needed as network transformers in order to ensure the meltability of the glass. These glasses as well are not contemplated for use as dental glasses, since they lack by far the requisite radiopacity. Apart from that, the content of $Al_2O_3$ raises the viscosity of the high-$SiO_2$-content glass and therefore necessitates high melting temperatures for the purpose of production. High contents of MgO are a disadvantage in glasses for dental applications, which are intended to have low indices of refraction in conjunction with high radiopacity. MgO does not raise the radiopacity to the same extent as the other alkaline earth metal oxides CaO, SrO and BaO, instead being manifested primarily in an increase in the index of refraction $n_d$, and it may therefore complicate the desired balance between low index of refraction and high radiopacity.

Features shared by all of the glasses identified in the prior art are that they either have low hydrolytic resistance or are too reactive and/or are not radiopaque, or they include components harmful to health and/or the environment. Many known dental glasses, moreover, contain SrO, which greatly increases the melting temperature. In addition to this economic disadvantage, a high SrO proportion makes for difficult-to-control crystallization operations during the production process of numerous glasses. With the known radiopacifiers, employed alone or in the known combinations (usually in combination with $La_2O_3$), the radiopacity achievable cannot be increased arbitrarily and satisfactorily without too great an increase in the refractive index. Glasses having a refractive index of greater than 1.65 can currently not be used satisfactorily in practice as dental glasses, fillers for polymer-based dental compositions (as described in WO 2007/034258 A1, for example). A disadvantage of lanthanum oxide, moreover, is that it is highly priced.

SUMMARY OF THE INVENTION

It is an object of the invention to provide a lead-free, radiopaque glass of relatively low refractive index, having an improved radiopacity.

In particular, it is also an object of the invention, for improved ease of production, to provide a glass system with which it is possible, within a given refractive index range, to produce glasses having a precisely defined index of refraction and, with regard to the index of refraction, improved radiopacity more easily. The glass is to be suitable preferably for use in the medical sector, especially in the dental sector as dental glass, and as optical glass. It is to be rationally producible and nevertheless of high-grade and biocompatible, and also to be suitable for passive and active dental protection, and is to have excellent properties in terms of processability, the setting behaviour of surrounding polymer matrices, and also the long-term stability and the strength. In order to meet the requirements in modern dental treatment and dental technology, moreover, the glass according to the invention must have at least good hydrolytic stability.

The glass according to the invention in its basic matrix, furthermore, is to be free from colouring components such as $Fe_2O_3$, CoO, NiO, CuO etc., for example, apart from impurities at most or importations and/or residual constituents that are difficult to avoid in industrial production, in order so to enable an optimum starting colour location for possible adaptations to the tooth colour and/or, in the case of optical applications, to enable the adaptation of the spectrum of the electromagnetic radiation that passes through. Moreover, the glass is to be free from a second glass phase and/or from colouring particles which lead to scattering and likewise modify the perceived colour. One or more further glass phases would lower the resistance of the glass.

The object is achieved by the glass according to the independent claims. Preferred embodiments and applications are apparent from the dependent claims.

Provided in particular is a radiopaque glass having a refractive index $n_d$ of 1.48 to 1.56, being free from PbO apart from impurities at most, comprising (in wt % based on oxide)

| | |
|---|---|
| $SiO_2$ | 35-75 |
| $B_2O_3$ | 5-15 |
| $Al_2O_3$ | 0.8-7.5 |
| $K_2O$ | 0-10 |
| BaO | 0.6-24 |
| $Cs_2O$ | 1-30 |
| $SnO_2$ | 1-15 |
| F | ≥0.5 |
| $BaO + Cs_2O + SnO_2 + F$ | ≥10. |

The glass according to the invention has a refractive index $n_d$ (also called index of refraction) of 1.48 to 1.56. It is therefore very well adapted to the available dental polymers and/or acrylate-based resins in this refractive index range, thereby satisfying the aesthetic requirements imposed on a polymer-based dental composition, especially on a dental glass/polymer composite, for appearance to be natural.

The glass according to the invention achieves the properties of lead-containing dental glasses in relation to the requisite X-ray absorption without using lead or other substances objectionable on health grounds. The glass according to the invention is lead-free. The term "free from" in this context denotes an absence of these substances apart from unavoidable contamination at most, that may be caused, for example, by air contamination and/or impurity in raw materials employed. However, even contamination of the glass with the unwanted substances is in general not to exceed 300 ppm for $Fe_2O_3$, preferably not more than 100 ppm, 30 ppm for PbO, 20 ppm for $As_2O_3$, 20 ppm for $Sb_2O_3$, and 100 ppm for other impurities. SRO is always closely associated with the BaO in the raw material. Depending on the purity of the BaO raw material, there may be up to 0.7 wt % of SrO in the glass according to the invention. These limits are embraced by the wording "apart from impurities at most, free from". Particularly preferred, of course, is the complete absence of the stated unwanted substances from the glass according to the invention. No SrO component is actively added, preferably, to the glass according to the invention.

The X-ray absorption and therefore the radiopacity is achieved in accordance with the invention through the combination of BaO, $Cs_2O$ and $SnO_2$. Unlike earlier dental glasses, which attempted to achieve radiopacity usually through the high content of, as far as possible, one high absorbing component, or through a combination with $La_2O_3$, the radiopacity in accordance with the invention is achieved by the appropriate combination of these BaO, $SnO_2$ and $Cs_2O$ components, which are effective for the radiopacity. In this way it is possible to attain the particularly stringent requirements for the optical properties of the glass, and also to achieve the very good hydrolytic and/or chemical resistance. Preferred for the content of BaO, $SnO_2$ and $Cs_2O$ are in total at least 8 wt %, more preferably at least 10 wt %, very preferably at least 12 wt %. If the total amount of these latter components is too small, X-ray absorption is not sufficiently strong. The higher the sum of these radiopacifiers in the glass, the higher is the radiopacity as well. An advantageous upper limit for the sum of BaO, $SnO_2$ and $Cs_2O$ may be 51 wt %, preferably 49 wt %, more preferably 47 wt %, also preferably 45 wt %, further preferably 43 wt %.

In accordance with the invention, furthermore, the radiopaque glass comprises a defined amount of fluorine, serving to specifically adjust the refractive index of the glass depending on the particular amount of radiopacifiers. This counteracts the effect whereby, as a. result of using a larger quantity of radiopacifier in the glass, the radiopacity is indeed increased, but at the same time the refractive index of the resulting glasses goes up. Through the addition of fluorine it is possible to maintain within limits the increase in the refractive index, or even to prevent the increase in the refractive index.

The combination of the radiopacifying components BaO, $Cs_2O$, and $SnO_2$ with F has proved, surprisingly, to be particularly suitable for creating glasses which have a high radiopacity in the relatively wide refractive index range from 1.48 to 1.56. In the context of the invention, provision is made for this purpose for the sum of BaO, $Cs_2O$, $SnO_2$ and F in wt % based on oxide to be at least 10 wt %, advantageously at least 12 wt %, preferably at least 14 wt %, more preferably at least 17 wt %. An advantageous upper limit for the sum of BaO, $Cs_2O$, $SnO_2$ and F may be 56 wt %, preferably 54 wt %, more preferably 52 wt %, also preferably 50 wt %, and most preferably 48 wt %. It is common knowledge that glasses having a lower index of refraction tend to be able to achieve a lower radiopacity and correspondingly lower values of aluminium equivalent thickness than glasses having a higher index of refraction. The reason for this is that for low-index glasses only relatively low amounts of radiopacifiers can be used. If the proportion of the radiopacifiers were increased, the refractive index would shift to higher values. Through the combination of BaO, $Cs_2O$, and $SnO_2$ with F in accordance with the invention it is possible to shift the radiopacity of the glasses and, correspondingly, the aluminium equivalent thickness to higher values over the whole refractive index range according to the invention. This means that for a given index of refraction, it is possible to achieve substantially higher X-ray visibility values than was hitherto possible. It is possible, moreover, to specifically adjust the index of refraction in a radiopaque glass.

All in all, success has been achieved with the invention in providing a glass system which allows the refractive index of the glass to be precisely adjusted to the particular requirements by varying the proportions of the components within the stated system, wherein the glass has an improved radiopacity for a given refractive index. This simplifies the production of differently refracting glasses with high radiopacity.

As a basis, the glass according to the invention comprises $SiO_2$ with a proportion of 35 to 75 wt % as glass-forming component. The upper limit in accordance with the invention is 75 wt %. Higher contents of $SiO_2$ may lead to disadvantageously high melting temperatures, whereas, moreover, the requisite radiopacity cannot be achieved. In the case of advantageous embodiments, 73 wt %, preferably 70 wt %, more preferably 68.5 wt % may be selected as an $SiO_2$ upper limit. In accordance with the invention, the lower limit is 35 wt %. Lower contents may have adverse consequences for the chemical resistance and the devitrification tendency. The $SiO_2$ lower limit in the case of an advantageous glass composition may be 36 wt %, preferably 37 wt %, more preferably 38 wt %, further preferably 39 wt %. One preferred embodiment of the glass according to the invention envisages a $SiO_2$ content of 38 to 70 wt % and more preferably of 39 to 70 wt %.

$B_2O_3$ is provided in the glass according to the invention with a content of 5 to 15 wt %. It may be present advantageously in the range from 6 to 15 wt %. $B_2O_3$ has a positive influence on glass formation and on melting behaviour. It also acts as a flux. Apart from the lowering effect on the melting temperature, the use of $B_2O_3$ leads at the same time to an improvement in the crystallization stability of the glass according to the invention. In accordance with the invention, therefore, the lower limit is 5 wt %. For certain glasses, 6 wt %, preferably 7 wt %, may also be selected as an advantageous lower limit for boron oxide. The upper limit for boron oxide in accordance with the invention is 15 wt %. Higher proportions are not recommended in this system, so as not to jeopardise the chemical resistance. A maximum of 14.5 wt %, preferably a maximum of 14 wt %, of boron oxide may also advantageously be included. If contents of $B_2O_3$ are too high, there may be instances of separation in the glass, which in turn represent an unwanted inhomogeneity of refractive index and, moreover, have adverse effects on the chemical resistance.

The glass according to the invention necessarily includes $Al_2O_3$ in the range from 0.8 to 7.5 wt %. It may be present advantageously in the range from 1 to 7 wt %. $Al_2O_3$ improves the chemical resistance of the glass. In accordance with the invention, therefore, it is present at not less than 0.8 wt % in the glass. At least 1 wt %, preferably at least 1.2 wt % of aluminium oxide may also advantageously be used. However, an $Al_2O_3$ content of around 7.5 wt % ought not to be exceeded, so as not to increase the viscosity of the glass—especially in the hot processing area—to such an extent that the glass is difficult to melt. Moreover, excessively large amounts of aluminium oxide impair the devitrification tendency and also the resistance of the glass towards acids. The upper limit of $Al_2O_3$ is preferably 7 wt %, more preferably indeed just 6.5 wt %.

Alkali metal oxides from the group of $Li_2O$, $Na_2O$ and $K_2O$ may be needed in order for the glass to be able to be melted at all. $K_2O$ serves for adjustment of the melting temperatures and at the same time strengthens the glass network. In accordance with the invention, therefore, it is present with a proportion of 0 to 10 wt % in the glass composition. For $K_2O$ the range from 0 to 7 wt % is preferred, from 0 to 5 wt % particularly preferred. The upper limit of 10 wt % for $K_2O$ in accordance with the invention ought not to be exceeded, since the content of alkali metal oxides lowers the chemical resistance. Advantageously, also 7 wt %, preferably 5 wt %, more preferably 4 wt % may be selected as an upper limit.

Sodium ions and lithium ions have a small size which renders them more readily leached out of the glass matrix, thereby diminishing the chemical resistance, especially the hydrolytic resistance. In one advantageous embodiment of the invention, the radiopaque glass is free from $Na_2O$ and/or $Li_2O$ apart from impurities at most.

Impurities may be introduced into the glass by contamination of the raw materials used for glass production, and/or by contamination and/or corrosion of the melting assemblies employed. Such impurities generally do not exceed a proportion of 0.2 wt %, especially 0.1 wt %. This also, of course, includes the complete absence of the component in question.

"Free from a component" therefore means that the glass essentially does not contain this component, i.e. that any such component is present as an impurity at most in the glass, but is not added as an individual component to the glass composition.

BaO, $Cs_2O$ and $SnO_2$ are always present in the glass according to the invention and, in combination, they ensure a high radiopacity of the glass.

The content of barium oxide is 0.6 to 24 wt %. A preferred range is that from 0.8 to 20 wt %, more preferably from 1 to 18.5 wt %. Too high an amount of BaO leads to the deterioration of the chemical resistance. The upper limit of 24 wt % ought therefore not to be exceeded. As an upper limit it is also possible to select, advantageously, 22 wt %, more advantageously 20 wt %, preferably 18.5 wt %. At least there ought to be 0.6 wt % of BaO present in the glass, in order to acquire, together with the other substances, the X-ray absorption. BaO may be present in the glass advantageously at not less than 0.8 wt %, preferably not less than 1 wt %, more preferably not less than 1.1 wt %.

$Cs_2O$ in accordance with the invention is likewise used to establish the X-ray visibility, but at the same time also contributes to improving the meltability. In accordance with the invention, $Cs_2O$ is present in the glass composition at 1 to 30 wt %, preferably 1 to 28 wt %, more preferably 1.5 to 26 wt %, and very preferably 2 to 25 wt %. The alkali metal Cs is more immobile in a glass matrix by comparison with the alkali metals Li, Na, K and Rb. It is therefore leached less severely and so detracts less from the chemical resistance than do the aforementioned alkali metals. Since too small an amount of $Cs_2O$ results in poorer X-ray visibility and increased melting temperatures, the lower limit according to the invention is 1 wt %. In the case of an advantageous glass composition, the lower limit may also be 1.5 wt %, more advantageously 2 wt %, preferably 2.5 wt %, very preferably 3 wt %. In accordance with the invention there ought to be not more than 30 wt % of $Cs_2O$ present, since otherwise the chemical resistance is impaired. An advantageous glass composition contains not more than 28 wt % of $Cs_2O$, preferably not more than 26 wt % of $Cs_2O$, more preferably not more than 25 wt % of $Cs_2O$.

$SnO_2$ serves likewise, in accordance with the invention, for adjusting the X-ray visibility. It contributes to a high radiopacity, with the index of refraction being increased less strongly than in the case of other radiopacifiers. This component is present in the glass composition with a proportion of 1 to 15 wt %, advantageously 3 to 15 wt %, preferably 4 to 15 wt %, more preferably >4 to 15 wt %, very preferably 4 to 12 wt %, especially preferably 4-10 wt %. Too small an amount of $SnO_2$ leads to poor X-ray visibility, and so this component ought to be present at not less than 1 wt %. Moreover, $SnO_2$ improves and secures the chemical resistance of the $Cs_2O$-containing glass. As an $SnO_2$ lower limit, 3 wt %, preferably 4 wt %, more preferably >4 wt % may advantageously also be provided. Too high an amount of $SnO_2$ results in severe devitrification and/or crystallization tendency. The upper limit of 15 wt % ought therefore not to be exceeded. Selected as an upper limit there may also be, advantageously, 13 wt %, preferably 12 wt %, more preferably 10 wt %, very preferably also 9 wt % of $SnO_2$.

In the context of the invention, the radiopaque glass contains fluorine with a proportion of at least 0.5 wt %. Present advantageously is at most 5 wt %, preferably at most 2.5 wt %. Advantageous ranges for F may also be 0.75 to 2.5 wt %, particularly advantageously from 0.75 to 2.25 wt %, preferably 1 to 2 wt %. Fluorine here is reported in atomic form, referred to the mass, in the composition. It serves for adjusting the refractive index in interaction with the above-described combination of radiopacifiers, and improves the melting characteristics of the glass batch by lowering the melting temperatures. It ought therefore to be included at not less than 0.5 wt % in the composition. 0.75 wt % as well, preferably 1 wt %, may be selected as an advantageous lower limit. The upper limit of 5 wt % ought not to be exceeded, since otherwise the component may evaporate during the melting operation and there may be an inhomogeneous distribution of index of refraction in the glass. Fluorine may also advantageously be present with a proportion of at most 2.5 wt %, preferably at most 2.25 wt %, more preferably at most 2 wt %.

At this point it may be noted that, in a manner evident to the skilled person and embraced by the present description, any of the stated upper and/or lower limits of one component may be combined arbitrarily with every stated upper and/or lower limit of another component.

In one advantageous embodiment of the glass, provision is made for the molar ratio of $SnO_2$ to F to be at least 0.4, preferably at least 0.45, more preferably at least 0.49, very preferably at least 0.5. The molar ratio of $SnO_2$ to F in the advantageous embodiment is at most 0.85, preferably at most 0.79, more preferably at most 0.77, with further preference at most 0.75, also preferably at most 0.72, very preferably at most 0.7. When this condition is satisfied it is possible to set the index of refraction of the glass precisely in conjunction with a relatively high X-ray absorption. A further advantage is that a ratio within the aforesaid range ensures that the glass has good meltability properties. Too high a value of the ratio results in inhomogeneous melts.

In order to improve further the adjustment of index of refraction and radiopacity, i.e. high aluminium equivalent thickness, in the radiopaque glass, it is advantageous if the molar ratio of $Cs_2O$ to the sum of the above-stated opacifiers $Cs_2O$, BaO and $SnO_2$ is at least 0.05, preferably at least 0.07, more preferably at least 0.1. It is advantageous not to exceed an upper limit of 0.48, preferably of 0.45, more preferably of 0.41. Too small a ratio leads to too low X-ray absorption. Too high a ratio reduces the chemical resistance.

The radiopaque glass may optionally contain $ZrO_2$ with a proportion of 0 to 2 wt %, preferably 0 to 1 wt %. This zirconium content improves the mechanical properties, and particularly the tensile strength and compressive strength, and also lowers the brittleness of the glass. Contents which are too high, however, may result in the glass becoming highly reactive, particularly in the environment of dental polymers. The glass, in contrast, is to be at least very largely inert towards dental polymers, especially composites, and is for example not to interfere with their polymerization behaviour. In one advantageous variant, the glass is free from zirconium oxide ($ZrO_2$-free).

One advantageous embodiment of a radiopaque glass may comprise a limited proportion of alkaline earths from the CaO and MgO group. The proportion of CaO may be 0 to 2 wt %. MgO is likewise optional and may be present at from 0 to 2 wt %. In one especially preferred embodiment, the glass according to the invention is free from MgO, apart from impurities at most. MgO may be disadvantageous in glasses for dental applications, which are to combine low refractive indices with high radiopacity. MgO does not raise the radiopacity to the same extent as the other alkaline earth metal oxides CaO, SrO and BaO, because the X-ray absorption edge of MgO is well below theirs, and exhibits only a little influence in the area of the tungsten X-ray tubes used in the medical sector. MgO would merely increase the index of refraction and thereby complicate the balance between low index of refraction and high radiopacity.

The glass according to the invention is envisaged to be free from $CeO_2$ and $TiO_2$, optionally, apart from impurities at most. On account of their absorption in the UV region, $CeO_2$ and $TiO_2$ shift the UV edge of the glass, which may consequently acquire an unwanted yellowish colouration. In one preferred embodiment, the glass according to the invention is $TiO_2$-free.

One particularly preferred embodiment of the glass is free from $TiO_2$ and $ZrO_2$.

ZnO and/or $WO_3$ and/or $Nb_2O_5$ and/or $HfO_2$ and/or $Ta_2O_5$ and/or $Gd_2O_3$ and/or $Sc_2O_3$ and/or $Y_2O_3$ and/or $Yb_2O_3$ and/or $La_2O_3$ may be additionally present preferably and optionally individually or in any combinations at 0 to 2 wt % in each case. The restriction of the $La_2O_3$ content has the advantageous effect that the refractive index of the glass is not increased too much. One preferred embodiment of the glass is free from $La_2O_3$. This offers cost advantages and allows the production of low-index glasses with high radiopacity.

It is possible for the radiopaque glass, for technical or optical applications, to comprise at least one refining agent, selected for example from the group of chlorides or sulphates, with a proportion of 0 to 2 wt %, advantageously of 0 to 1 wt %. $SnO_2$ as well can be used as a refining agent, with the advantage over refining agents that are likewise possible, such as $As_2O_3$ and $Sb_2O_3$, and also the stated chlorides and sulphates, that no contamination by other refining agents is carried into the melting assemblies. This is advantageous if, subsequent to technical glasses, dental glasses are produced again.

The linear coefficient of thermal expansion $\alpha_{(20-300)}$, measured in the temperature interval from 20° C. to 300° C., of the glass according to the invention is preferably less than $7\times10^{-6}$ $K^{-1}$. As a result of the low coefficient of thermal expansion, the glasses according to the invention, especially when used as filling material in polymers, are capable of compensating the natural, high thermal expansion of the polymers, thus giving the polymer-based dental composition a thermal expansion which is better adapted to the natural tooth material.

As already described, the glasses according to the invention are resistant to chemical attack—that is, they are chemically stable. They preferably have a water resistance HGB in accordance with DIN ISO 719 of Class 2 or better.

The glasses according to the invention are therefore notable all in all for good chemical resistance, resulting in a high degree of inertness in combination with the resin matrix, and thus with a very long lifetime of the dental composition as a whole.

According to a further preferred embodiment of the present invention, the glass according to the invention is also preferably free from other components not stated in the claims and/or in the present description. This means that according to one such embodiment, the glass substantially consists of the stated components. The expression "substantially consist" here means that other components are present as impurities at the most, but are not deliberately added as an individual component to the glass composition.

Nevertheless, the invention also envisages the use of the glass according to the invention as a basis for further glasses, in which up to 5 wt % of further components may be added to the glass according to the invention described. In such a case the glass consists, in accordance with the invention, of the glass described to an extent of at least 95 wt %.

It is, of course, also possible to adapt the coloured appearance of the glass for optical or other technical applications through the addition of oxides customary for the purpose. Oxides suitable for colouring glasses are known to the skilled person, examples including CuO and CoO, which for these purposes may be added preferably at from 0 to 0.5 wt %. Moreover, the glass may be given an antiseptic function through additions, for example, of $Ag_2O$ at 0 to 3 wt %.

The invention further encompasses glass powders composed of the glasses according to the invention, and the use of a radiopaque glass according to the invention as glass powder. The glass powders are produced by known methods, as described for example in DE 41 00 604 C1. The glass powder according to the invention and/or the powder particles preferably have an average particle size of up to 50 μm, more preferably up to 20 μm. An average particle size of 0.1 μm may be reached as a lower limit, wherein of course smaller particle sizes are also encompassed by the invention. The aforementioned glass powder may serve as starting material for the use of the glasses according to the invention as fillers and/or dental glasses in general. An advantageous use of a radiopaque glass according to the invention is in a dental glass/polymer dental composition comprising dental polymer. A dental composition of this kind finds use, for example, as dental filling material, material for inlays, onlays, dental cement, facing material for crowns and bridges, material for artificial teeth, and/or other material for prosthetic, preservative and/or preventive dental treatment.

In one preferred embodiment, the surface of the glass powder, i.e. the surface of the glass powder particles, is silanized by the customary techniques. Silanization makes it possible to improve the binding of the inorganic fillers to the polymer matrix of the polymer-based dental composition.

The object stated at the outset is further achieved by a radiopaque glass according to the invention for use in the medical sector, more particularly in the dental medical sector as dental glass, and/or for diagnostic purposes. Diagnostic purposes include medical applications, an example being use in a contrast medium.

Furthermore, the object stated at the outset is achieved by a radiopaque glass according to the invention for use as dental glass for treating cavities in human and/or animal teeth and/or for dental restoration. The treatment generally comprises complete or partial filling of a cavity, a hollow, a gap, etc., in a tooth.

The glass according to the invention may be used as described preferably as dental glass. In that case it is advantageous if the dental glass is in the form of powder particles. It is further advantageous if it is a constituent of a polymer-based dental composition comprising a dental polymer, more particularly forming a filler in powder form. The surfaces of the powder particles are preferably silanized. In one advantageous embodiment, further components may be admixed to the dental composition in addition to the glass powder, examples being a barium and/or strontium and/or lithium aluminate glass-ceramic powder, an addition for further increasing the radiopacity (e.g. ytterbium trifluoride and/or yttrium fluoride), or a filler for adjusting the viscosity (more particularly fumed and/or wet-precipitated silica).

The dental glass preferably finds application as a filler in composites (also called filling composites) for the treatment, more particularly the filling, of dental cavities and/or for dental restoration, more preferably for acrylate-based polymers, which require largely chemically inert fillers. Likewise within the context of the invention is the use of the glass according to the invention as a radiopacifier in dental compositions, especially polymer-based dental compositions. The glass according to the invention is a suitable replacement for expensive crystalline radiopacifiers such as $YbF_3$, for example. The glass according to the invention is also suitable and intended for use as a filler in dental cements, e.g. glass ionomer cements. It is likewise possible for the glass according to the invention to be used as an inert additive in glass ionomer cements. Particularly preferred is the use as an inert additive in polymer-reinforced glass ionomer cements. The polymer-reinforced glass ionomer cements comprise a class of materials available for the past few years, exhibiting per se the curing reaction of a cement, which may take a very long time, but also including a resin matrix like the composite described above, so as to be curable initially.

Correspondingly, the radiopaque glass according to the invention is used preferably for producing a dental glass/polymer composite comprising a dental polymer. The dental polymer preferably comprises a UV-curable resin based on acrylate, methacrylate, 2,2-bis[4-(3-methacryloyloxy-2-hydroxypropoxy)phenyl]propane (bis-GMA), triethylene glycol dimethacrylate (TEGDMA or TEGMA, depending on what is meant here), urethane dimethacrylate (UDMA), alkanediol dimethacrylate or cyanoacrylate.

Likewise encompassed by the invention is the use of the glass according to the invention as an optical element which comprises the glass according to the invention. Optical elements are understood to be all articles, and especially components, which may be employed for optical applications. These may be components through which light passes. Examples of such components are cover glasses and/or lens elements, but also supports of other components, such as mirrors and glass fibres, for example.

Cover glasses are used preferably for protecting electronic components. These, of course, likewise include optoelectronic components. The cover glasses are present customarily in the form of glass plates having plane-parallel surfaces and are preferably mounted above the electronic component, thereby protecting it from environmental effects, but allowing electromagnetic radiation such as light and X-radiation, for example, to pass through the cover glass and interact with the electronic component. For certain optoelectronic components, however, X-radiation may also be harmful. A cover glass produced from the radiopaque glass according to the invention may therefore be used for instances such as X-ray protective glass, for example, in medical apparatus.

A further possible application is the use of the radiopaque glass according to the invention as cover glass and/or substrate glass in display technology for cathode ray tubes (CRT).

On the basis of its optical properties, the glass according to the invention may likewise be used for optical applications. Being largely chemically inert, it is suitable for applications as substrate glass and/or cover glass in photovoltaics, as for example for the covering of silicon-based photovoltaic cells, of organic photovoltaic cells and/or as support material for thin-film photovoltaic modules. The X-ray absorption of the glass according to the invention has particular advantages, among others, in the use of photovoltaic modules in aerospace applications, since these modules may be exposed to particularly intense X-radiation outside the Earth's atmosphere. The property of the high X-ray absorption, moreover, allows the glass to be used, very generally, as X-ray protective glass.

By virtue of its high temperature stability, the glass according to the invention is also suitable as lamp glass, particularly for use in halogen lamps and/or fluorescent tubes and related constructions. If the mechanisms of light generation in the lamp give rise to X-radiation, a particular advantage of the glass according to the invention is that this radiation can be kept away from the surroundings. Furthermore, the glass according to the invention can be used in X-ray tubes.

Additionally encompassed by the invention is the vaporization of the glass according to the invention by physical methods and the deposition of the vaporized glass on components. Such physical vapour deposition processes, also called PVD processes for short, are familiar to the skilled person and described for example in DE 102 22 964 B4. In such processes, the glass according to the invention serves as the target to be vaporized. The components vapour-coated with the glass according to the invention may benefit both from the chemical resistance of the glass and from its X-ray absorption.

Furthermore, on account of their high stability, the glasses according to the invention are likewise suitable as matrix material for the secure temporary and/or permanent storage of radioactive waste, and also for the embedding of radioactive materials.

This glass also exhibits advantages in application as container glass or packaging for pharmaceutical products. In view of the high stability with respect to ambient media, interactions with ingredients can be almost ruled out.

The preceding description of the present invention is a summary of the present invention that provides an understanding of some aspects of the present invention. However this summary is neither completely extensive nor completely exhaustive. As will be appreciated, other embodiments and variations of the present invention, especially as defined by the claims appended herein below, are possible, utilizing, alone, or in combination, one or more of the above-described features and/or details set forth herein above.

EXAMPLES

The invention is illustrated below with examples which elucidate the teaching of the invention but are not intended to restrict it.

TABLE I

| | Working examples (AB) in wt % | | | | | | | |
|---|---|---|---|---|---|---|---|---|
| Example No. | AB1 | AB2 | AB3 | AB4 | A85 | AB6 | AB7 | AB8 |
| $SiO_2$ | 42.7 | 63.8 | 66.2 | 61.5 | 53.8 | 54.1 | 51.3 | 48.3 |
| $B_2O_3$ | 8.3 | 13.8 | 11.9 | 10.5 | 10.4 | 8.9 | 9.5 | 8.3 |
| $AlO_3$ | 3.6 | 1.3 | 4.7 | 6.3 | 5.2 | 5.9 | 5.0 | 4.9 |
| $K_2O$ | | 2.6 | 2.7 | 3.9 | 3.6 | 3.6 | 3.2 | 3.4 |
| $Cs_2O$ | 16.7 | 8.5 | 3.0 | 5.8 | 9.8 | 5.4 | 9.6 | 11.8 |
| BaO | 18.2 | 4.7 | 2.2 | 3.1 | 8.8 | 13.7 | 13.3 | 15.5 |
| $SnO_2$ | 8.9 | 4.2 | 7.5 | 7.2 | 6.7 | 6.7 | 6.5 | 6.3 |
| $ZrO_2$ | — | — | — | — | — | — | — | — |
| F | 1.6 | 1.1 | 1.9 | 1.8 | 1.7 | 1.7 | 1.6 | 1.6 |
| $Cs_2O$ + BaO + $SnO_2$ + F | 45.4 | 18.5 | 14.6 | 17.9 | 27.0 | 27.5 | 31.0 | 35.2 |
| Total | 100.0 | 100.0 | 100.0 | 100.0 | 100.0 | 100.0 | 100.0 | 100.0 |
| $n_d$ | 1.548 | 1.497 | 1.488 | 1.495 | 1.515 | 1.522 | 1.525 | 1.533 |
| Density (g/cm$^3$) | 3.15 | 2.49 | 2.36 | 2.46 | 2.67 | 2.71 | 2.78 | 2.90 |
| Rel. ALET (%) | 1240 | 420 | 310 | 410 | 670 | 690 | 800 | 940 |
| Hydrolytic class to DIN ISO 719 | | | | | | HGB1 | | HGB1 |
| Thermal expansion α (20-300° C.) ($10^{-6}$ K$^{-1}$) | 5.9 | 4.3 | | | 5.3 | | 5.9 | |

TABLE I-continued

| | Working examples (AB) in wt % | | | | | | |
|---|---|---|---|---|---|---|---|
| Example No. | AB9 | AB10 | AB11 | AB12 | AB13 | AB14 | AB15 |
| $SiO_2$ | 45.3 | 40.6 | 68.4 | 38.8 | 52.4 | 52.0 | 49.6 |
| $B_2O_3$ | 7.9 | 7.4 | 12.4 | 7.3 | 9.7 | 9.5 | 9.2 |
| $AlO_3$ | 4.1 | 3.3 | 4.8 | 3.2 | 3.8 | 5.1 | 4.9 |
| $K_2O$ | 2.4 | 3.0 | 2.7 | 2.9 | 0.8 | 3.3 | 3.1 |
| $Cs_2O$ | 15.3 | 24.0 | 3.1 | 25.0 | 9.8 | 8.0 | 9.3 |
| BaO | 15.8 | 12.2 | 1.1 | 12.8 | 15.6 | 13.5 | 12.9 |
| $SnO_2$ | 7.7 | 8.0 | 6.0 | 8.6 | 6.7 | 6.6 | 6.3 |
| $ZrO_2$ | — | — | — | — | — | 0.8 | — |
| F | 1.5 | 1.4 | 1.5 | 1.4 | 1.2 | 1.2 | 4.8 |
| $Cs_2O$ + BaO + $SnO_2$ + F | 40.3 | 45.6 | 11.7 | 47.8 | 33.3 | 29.3 | 33.3 |
| Total | 100.0 | 100.0 | 100 | 100 | 100.0 | 100.0 | 100.0 |
| $n_d$ | 1.543 | 1.553 | 1.481 | 1.559 | 1.527 | 1.526 | 1.504 |
| Density (g/cm³) | 3.00 | 3.14 | 2.4 | 3.24 | 2.83 | 2.79 | 2.75 |
| Rel. ALET (%) | 1130 | 1340 | 140 | 1395 | 830 | 783 | 775 |
| Hydrolytic class to DIN ISO 719 | | | | | | | |
| Thermal expansion α (20-300° C.) ($10^{-6}$ $K^{-1}$) | | | | | | | |

Table I encompasses working examples of the radiopaque glass of the invention in the preferred compositional range. All data pertaining to the composition is listed in wt %. The glasses contain the radiopacifier combination according to the invention, of $Cs_2O$, BaO and $SnO_2$, and additionally a defined amount of fluorine. The stated combination and fluorine together form the radiopacifier system according to the invention, with which the index of refraction in the range from 1.48 to 1.56 and the relative aluminium equivalent thickness in the range from approximately 120% up to more than approximately 1400% can be established.

All values for the relative aluminium equivalent thickness (ALET in %) that are listed in Table I, corresponding to X-ray absorption (XRO in %), were determined in a method based on DIN ISO 4049. The grey values determined in the image were measured using image processing software and used for determination of the X-ray absorption. Table I additionally lists the refractive indices $n_d$ and densities of the working examples.

The glasses described in the examples in Table I were produced as follows:

The raw materials for the oxides are weighed out and then thoroughly mixed. The glass batch is melted at about 1580° C. in a discontinuous melting assembly, then refined and homogenized. At a casting temperature of about 1600° C., the glass can be cast and processed as ribbons or in other desired dimensions. In a high-volume, continuous assembly, the temperatures can be reduced by at least about 100 K.

For further processing, the cooled glass ribbons were milled by means of the method known from DE 41 00 604 C1 to form a glass powder having an average particle size of not more than 10 μm. The glass properties were determined on glass bulks which had not been milled into powders. The glasses have good chemical resistance with respect to water.

Additionally listed in Table I is the chemical resistance of variants of the glass according to the invention. Given by way of example for two examples is the hydrolytic resistance class (HGB) according to DIN ISO 719. The glasses according to the invention, however, also attain good values for acid resistance according to DIN 12116 and for alkali resistance according to DIN ISO 695.

TABLE II

| | Comparative examples (VB) in wt % | | | | | | | |
|---|---|---|---|---|---|---|---|---|
| | Example No. | | | | | | | |
| | DE102011084501B3 | | | | | DE102009008951A1 | | |
| | wt % | | | | | | | |
| | VB1 | VB2 | VB3 | VB4 | VB5 | VB6 | VB7 | VB8 |
| $SiO_2$ | 59.66 | 61.14 | 59.91 | 63.28 | 64.00 | 56.26 | 52.69 | 52.09 |
| $B_2O_3$ | | | | 2.97 | 2.98 | 11.13 | 10.42 | 10.30 |
| $Al_2O_3$ | 0.86 | 0.88 | 0.89 | 1.58 | 2.28 | 5.40 | 5.06 | 5.00 |
| $Li_2O$ | | | 0.4 | | | | | |
| $Na_2O$ | 2.41 | 2.47 | 2.48 | 1.26 | 1.26 | 2.70 | 2.53 | 0.65 |
| $K_2O$ | 2.88 | 4.2 | 3.85 | 2.11 | 2.12 | 14.02 | 13.13 | 12.98 |
| $Cs_2O$ | 10.95 | 7.48 | 7.53 | 11.43 | 10.69 | 4.09 | 5.31 | 8.41 |
| CaO | | | 0.97 | 2.88 | 2.13 | | | |
| MgO | | | | | | | | |

TABLE II-continued

Comparative examples (VB) in wt %

| | | | | | | | | |
|---|---|---|---|---|---|---|---|---|
| SrO | 11.89 | 12.19 | 12.26 | 6.81 | 6.83 | | | |
| ZnO | | | | | | | | |
| La$_2$O$_3$ | 4.22 | 4.33 | 4.35 | 4.40 | 4.42 | | 8.59 | 4.38 |
| ZrO$_2$ | 7.13 | 7.31 | 7.36 | 3.28 | 3.29 | 6.42 | 2.27 | 4.82 |
| WO$_3$ | | | | | | | | |
| SnO$_2$ | | | | | | | | 1.38 |
| P$_2$O$_5$ | | | | | | | | |
| F | | | | | | | | |
| Total | 100.00 | 100.00 | 100.00 | 100.00 | 100.00 | 100.00 | 100.00 | 100.00 |
| n$_d$ | 1.548 | 1.555 | 1.538 | 1.532 | 1.530 | 1.522 | 1.530 | 1.526 |
| relative ALET (%) | 763 | 679 | 684 | 638 | 617 | 276 | 395 | 472 |

Example No.

| | DE 102005051387B3 | | | DE19849388C2 | | U.S. Pat. No. 5,641,347 | |
|---|---|---|---|---|---|---|---|
| | wt % | | | | | | |
| | VB9 | VB10 | VB11 | VB12 | VB13 | VB14 | VB15 |
| SiO$_2$ | 58.00 | 63.00 | 58.00 | 38 | 23 | 64.0 | 70.0 |
| B$_2$O$_3$ | 2.00 | 0.10 | 10.00 | 10 | 10 | | |
| Al$_2$O$_3$ | 14.00 | 12.40 | 14.00 | 12 | 12 | | |
| Li$_2$O | | | | | | | |
| Na$_2$O | | | | 2 | 7 | 20.0 | 25.0 |
| K$_2$O | | | | | | | |
| Cs$_2$O | | | | | | | |
| CaO | 2.00 | | | | | | |
| MgO | 7.93 | 10.40 | 6.10 | | | | |
| SrO | | | | | 10 | | |
| ZnO | 2.50 | | | 6 | 6 | | |
| La$_2$O$_3$ | 1.57 | 8.20 | 1.50 | 4 | 4 | | |
| ZrO$_2$ | 2.00 | 3.90 | 0.40 | 3 | 3 | 16.0 | 5.0 |
| WO$_3$ | 10.00 | 2.00 | 10.00 | | | | |
| SnO$_2$ | | | | | | | |
| P$_2$O$_5$ | | | | 5 | 10 | | |
| F | | | | 20 | 15 | | |
| Total | 100.00 | 100.00 | 100.00 | 100 | 100 | 100.0 | 100.0 |
| n$_d$ | 1.534 | 1.548 | 1.512 | 1.514 | 1.535 | 1.548 | 1.513 |
| relative ALET (%) | 352 | 276 | 263 | 315 | 365 | 190 | 125 |

TABLE III

Comparative examples (VB) in mol %
From EP 1 547 572 A1

| Oxide | VB16, mol % | VB17, mol % | VB18, mol % | VB19, mol % |
|---|---|---|---|---|
| SiO$_2$ | 75 | 74 | 80 | 85 |
| Li$_2$O | | | | |
| Na$_2$O | 11 | 16 | 12 | 12 |
| K$_2$O | | | | 4 |
| Al$_2$O$_3$ | | | | |
| B$_2$O$_3$ | 4 | | | |
| MgO | | | | |
| SrO | | | | |
| La$_2$O$_3$ | | | | |
| Y$_2$O$_3$ | 10 | | | |
| ZrO$_2$ | | 10 | 4 | 3 |
| TiO$_2$ | | | | |
| Total | 100 | 100 | 100 | 100 |
| n$_d$ | 1.52 | 1.54 | 1.50 | 1.49 |
| relative ALET [%] | 200 | 120 | 190 | 80 |

Tables II and III list, for comparison, the compositions, refractive indices and the relative aluminium equivalent thicknesses in % (i.e. the X-ray absorption, XRO, in %) of comparative examples. The glasses are known dental glasses and radiopaque glasses and/or fillers for use in dental compositions, in which the radiopacity derives in each case from various radiopacifier systems (use of individual radiopacifiers and/or a combination of different radiopacifiers).

BRIEF DESCRIPTION OF THE DRAWING

The objects, features and advantages of the invention will now be illustrated in more detail with the aid of the following description of the preferred embodiments, with reference to the accompanying figures in which:

FIG. 1 shows in graph form the advantageous correlation between refractive index and relative aluminium equivalent thickness (relative ALET) for the working examples:

It is advantageous if, within the claimed refractive index range from 1.48 to 1.56, the refractive index is assigned a relative aluminium equivalent thickness ALET (in %), as may be described by the following equation:

relative ALET (%)=(15480 to 15900)*$n_d$−(23015 to 22695).

According to a first advantageous variant of the invention, it is advantageous if the radiopaque glass with a refractive index $n_d$ in the refractive index range between 1.48 and 1.56 has a relative aluminium equivalent thickness ALET (%) which is greater than or equal to a minimum relative aluminium equivalent thickness (min. relative ALET) which is defined by the following equation:

min. relative ALET (%)=$C$*$n_d$−$D$, where $C$=11000 and $D$=16160.

It is further advantageous if the radiopaque glass with a refractive index $n_d$ in the refractive index range between 1.48 and 1.56 has a relative aluminium equivalent thickness ALET (%) which is less than or equal to a maximum relative aluminium equivalent thickness (max. relative ALET) which is determined by the equation:

max. relative ALET (%)=$A$*$n_d$−$B$, where $A$=11430 and $B$=16230.

For the radiopaque glasses, therefore, advantageously, every refractive index in the $n_d$ range 1.48 to 1.56 may be assigned an interval of the relative ALET which is bounded by a maximum relative ALET and a minimum relative ALET. A radiopaque glass according to the invention having a defined refractive index $n_d$ has a relative ALET which lies advantageously in the interval of the relative ALET, the interval being calculable by the equations stated above.

Figure 2:
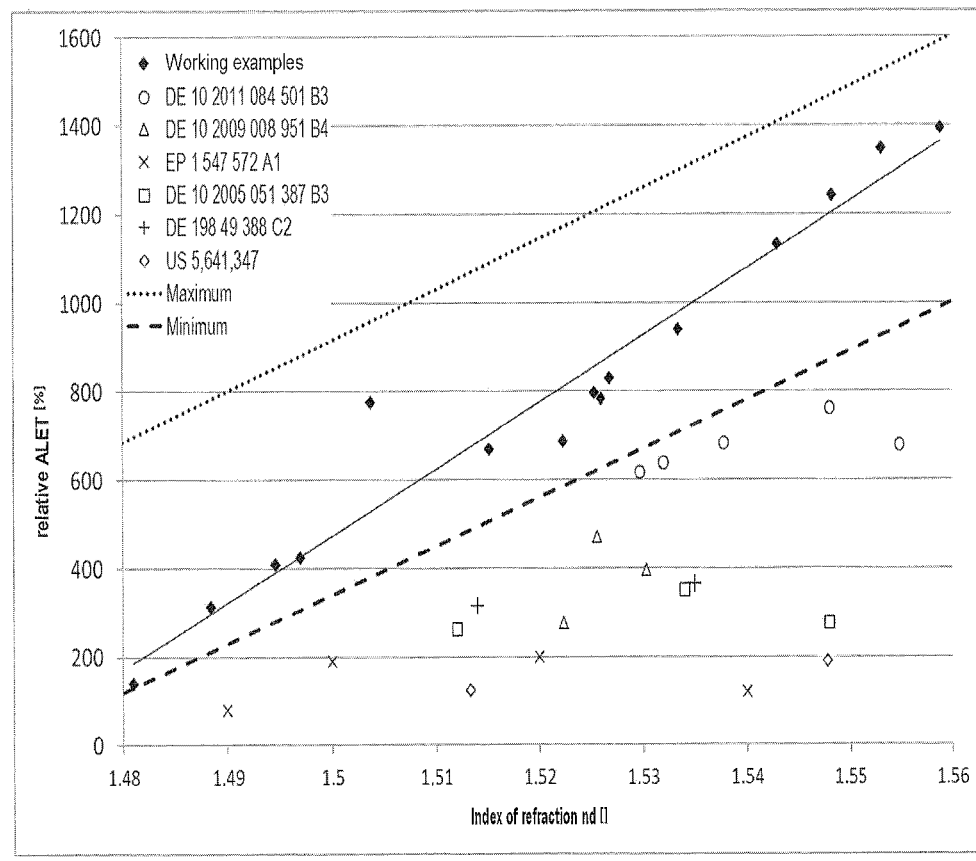
FIG. 2 is a graph illustrating two linear equations for upper and lower limits of the relative ALET.

According to this first advantageous variant, the assignment ($n_d$; relative ALET) is made by the establishing of two linear equations which define the advantageous upper and lower limits of the relative ALET in the $n_d$ range from 1.48 to 1.56 for the glasses according to the invention. FIG. 2 shows the graphs of the linear equations. The graphs form what are called "enveloping lines". In the region between the upper enveloping line (maximum) and the lower enveloping line (minimum), the advantageous range of the relative ALET, which is assigned to the $n_d$ range from 1.48 to 1.56, is located for the glasses according to the invention. As can be seen, the working examples are located between the "enveloping lines".

According to a second advantageous variant of the invention, in the refractive index range between 1.48 and 1.56, the assignment between the refractive index $n_d$ of the glass and the relative aluminium equivalent thickness ALET (%) is made via the statement of the following intervals:

| $n_d$ | ALET min. | and preferably | ALET max. |
|---|---|---|---|
| 1.48 to <1.49 | 120% | and preferably | 700% |
| 1.49 to <1.51 | 260% | and preferably | 1000% |
| 1.51 to <1.53 | 520% | and preferably | 1200% |
| 1.53 to <1.55 | 780% | and preferably | 1500% |
| 1.55 to 1.56 | 850%, preferably 910% | and preferably | 1600% |

What this means, to give an example, is as follows: a radiopaque glass having a composition in accordance with the invention and a refractive index which is within the $n_d$ range between 1.49 to <1.51 (e.g. $n_d$=1.50) advantageously has a relative ALET which is at least 260% (corresponding to ALET min.). At maximum, the ALET of this glass may be preferably 1000% (corresponding to ALET max.). For radiopaque glasses which fall within other $n_d$ ranges, the other values indicated in each case for "ALET min." and "ALET max." are valid. "ALET min." therefore defines a lower limit, and "ALET max." an upper limit, for the relative ALET, referred to a defined $n_d$ range.

According to an alternative advantageous variant, in the refractive index range between 1.48 and 1.56, the assignment between the refractive index $n_d$ of the glass and the relative aluminium equivalent thickness ALET (%) is made via the statement of the following intervals:

| $n_d$ | ALET min. | and preferably | ALET max. |
|---|---|---|---|
| 1.48 to <1.49 | 120% | and preferably | 760% |
| 1.49 to <1.50 | 240% | and preferably | 875% |
| 1.50 to <1.51 | 360% | and preferably | 990% |
| 1.51 to <1.52 | 475% | and preferably | 1105% |
| 1.52 to <1.53 | 590% | and preferably | 1220% |
| 1.53 to <1.54 | 705% | and preferably | 1335% |
| 1.54 to <1.55 | 820% | and preferably | 1450% |
| 1.55 to 1.56 | 935% | and preferably | 1565% |

What this means, to give an example, is as follows: a radiopaque glass having a composition in accordance with the invention and a refractive index which is within the $n_d$ range between 1.48 to <1.49 (e.g. $n_d$=1.485) advantageously has a relative ALET which is at least 120% (corresponding to ALET min.). At maximum, the ALET of this glass may be preferably 760% (corresponding to ALET max.). For radiopaque glasses which fall within other $n_d$ ranges, the other values indicated in each case for "ALET min." and "ALET max." are valid. "ALET min." therefore defines a lower limit, and "ALET max." an upper limit, for the relative ALET, referred to a defined $n_d$ range.

For gathering the data, glass bulks were produced from the glass compositions of the working examples, and the associated parameters were ascertained: the relative aluminium equivalent thickness (in %) was determined by the technique described above. The refractive index $n_d$ was determined in a known way. The number of samples per working example was 2. Each parameter was measured multiply, and the average values were calculated for the refractive index and the X-ray absorption. Linear regression allows the correlation between index of refraction and radiopacity to be represented for the radiopaque glasses according to the invention with the radiopacifier system of $SnO_2$, $BaO$, $Cs_2O$ and F, as shown in FIG. 1.

Figure 1:
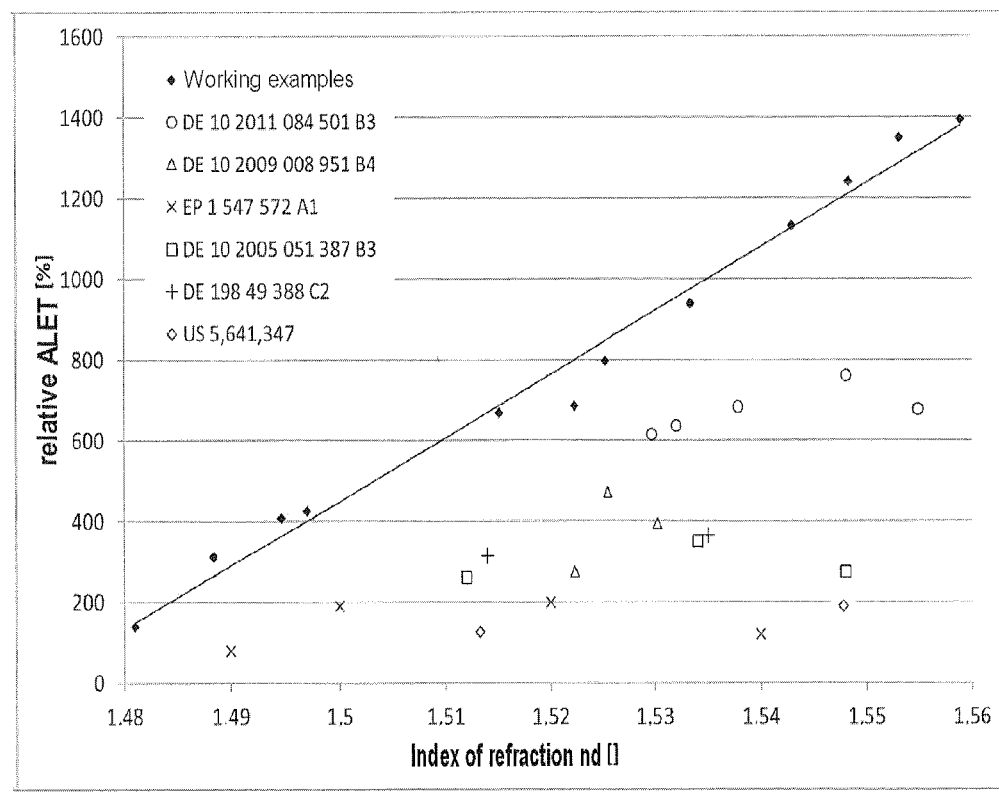
FIG. 1 is a graph showing the correlation between relative ALET and refractive index, $n_d$, for working examples of the radiopaque glass according to the invention.

For comparison, index of refraction and relative aluminium equivalent thickness are likewise plotted in FIG. 1 for the stated comparative examples, which are based on different radiopacifier systems. It can be seen that the working examples in the claimed refractive index range have a much higher X-ray absorption than the comparative examples (based on the respective refractive index). For the same index of refraction, X-ray absorption values achieved in the glasses according to the invention are substantially higher—for example, at $n_d$=1.548, working example AB1 has a relative ALET of 1240%, while comparative example VB1 has only 763%, comparative example VB10 only 276%, and comparative example VB14 only 190%. In the low index of refraction range as well, at around 1.49, working example AB3 exhibits a relative ALET of 310%, whereas that of comparative example VB19 is only 80%. Accordingly, the X-ray visibility of the glasses according to the invention, and of a polymer-based dental composition produced using them, is significantly increased. Accordingly, for the same thickness, optical elements (e.g. glass protective elements, etc.), comprising the glass according to the invention absorb more X-radiation as known optical elements or else, for the same X-ray absorption, can be made thinner, thereby allowing a weight saving to be made.

Especially in the case of glasses with low indices of refraction, it was hitherto difficult to raise the radiopacity, and possible only to raise it insufficiently, because increasing the proportion of radiopacifiers would have increased the index of refraction at the same time. With the radiopacifier system according to the invention, comprising $SnO_2$, BaO, $Cs_2O$ and F, a significant rise in the radiopacity is achieved even at low indices of refraction, and, in the higher index of refraction range, the aluminium equivalent thickness is improved very greatly relative to the known glasses.

In FIG. 2, working example AB15, in relation to the radiopacifier components $Cs_2O$, BaO and $SnO_2$, exhibits a similar composition and a similarly high relative ALET as working example AB7, but with a refractive index of 1.504 has a much lower refractive index than working example AB7 ($n_d$=1.525). This is attributable to the advantageous influence of the inventive fluorine component, allowing the refractive index to be adjusted specifically—and in this particular case, to be lowered. As a result it is possible specifically to produce a glass having a high relative ALET and a comparatively low refractive index.

A comparison of working examples AB13 and AB14, which are likewise shown in FIG. 2, makes it clear that through appropriate choice of the radiopacifiers in the radiopacifier system according to the invention, comprising $SnO_2$, BaO, $Cs_2O$ and F, it is possible to produce glasses having approximately the same refractive index but having different relative ALETs.

The invention may be additionally described by the following declarations as well:
1. Dental composition or dental material, comprising a radiopaque glass according to the invention as filler, for the treatment, more particularly for the filling, of cavities in human and/or animal teeth and/or for dental restoration.
2. Glass powder comprising powder particles composed of the radiopaque glass according to the invention.
3. Glass powder according to declaration 2, wherein the surfaces of the powder particles present are silanized.
4. Filler for polymer-based dental compositions for the treatment, more particularly filling, of cavities in human and/or animal teeth and/or for dental restoration, comprising the glass according to the invention.
5. Polymer-based dental composition comprising the radiopaque glass according to the invention or a glass powder composed of the glass according to the invention.
6. Dental glass/polymer composite comprising the radiopaque glass according to the invention or a glass powder composed of the glass according to the invention.
7. Dental glass/polymer composite according to declaration 6, wherein the dental polymer is preferably a UV-curable resin based on acrylate, methacrylate,2,2-bis[4-(3-methacryloyloxy-2-hydroxypropoxy)-phenyl] propane (bis-GMA), triethylene glycol dimethacrylate (TEGDMA or TEGMA, depending on what is meant here), urethane dimethacrylate (UDMA), alkanediol dimethacrylate or cyanoacrylate.
8. Dental glass/polymer glass ionomer cement comprising the radiopaque glass according to the invention or a glass powder composed of the glass according to the invention.
9. Use of a radiopaque glass according to the invention as dental glass for producing a dental glass/polymer dental composition comprising dental polymer for the treatment, more particularly filling, of cavities in human and/or animal teeth and/or for dental restoration.
10. Use of a radiopaque glass according to the invention as glass powder.
11. Use according to declaration 10, wherein the surfaces of the powder particles present are silanized.
12. Use according to declaration 10 or 11 in a dental glass/polymer dental composition comprising dental polymer.
13. Use of a radiopaque glass according to the invention as
    radiopacifier in a polymer-based dental composition and/or as
    element for optical applications and/or as
    cover glass and/or substrate glass in display technology for cathode ray tubes (CRT) and/or as
    cover glass and/or substrate glass in photovoltaics and/or as
    lamp glass in X-ray tubes and/or as
    material for the embedding of radioactive materials.

With the radiopacifier combination according to the invention ($SnO_2$, BaO, $Cs_2O$) and with the defined addition of fluorine it is possible to formulate a glass having on the one hand a desired index of refraction and on the other hand an extremely high X-ray absorption. In accordance with the invention, in the refractive index range from 1.48 to 1.56, it is possible to realize a range of the relative aluminium equivalent thickness from about 120% up to more than 1400%, e.g. up to 1600%.

The examples also demonstrate that the refractive indices $n_d$ of the glass system according to the invention, particularly in a range from 1.48 to 1.56, can be adapted to the intended application without detriment to the necessary ALETs. As a result, the system can be used advantageously in particular as a filler in dental compositions, but also for other applications which impose high requirements on factors including the purity and/or the chemical resistance and temperature stability. The glass system can be produced at favourable cost on an industrial scale.

The glass according to the invention, furthermore, is relatively easy to melt and therefore efficient to produce. Found in particular has been a glass system in which, through changes in the individual constituents within the stated limits, it is possible to adjust the refractive index in line with the requirements of the application—for example, requirements asked of a dental filling material—with the resulting glass having an improved ALET. The variation of the possible refractive indices encompassed by the invention is relatively wide. This glass system permits especially rational industrial production of glasses within the glass system, especially since only a defined selection of raw materials need be held in stock, within which the proportions are varied in the stated amounts. Accordingly, the procedural regimes when melting the glasses within the glass system are also very similar.

While the invention has been illustrated and described as embodied in a radiopaque glass and uses thereof, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

What is claimed is:

1. A radiopaque glass having a refractive index $n_d$ of 1.48 to 1.56, which is free of PbO apart from at most impurities, said radiopaque glass having a composition comprising, in wt. % on an oxide basis:

| | |
|---|---|
| $SiO_2$ | 35-75 |
| $B_2O_3$ | 5-15 |
| $Al_2O_3$ | 0.8-7.5 |
| $K_2O$ | 0-10 |
| BaO | 0.6-24 |
| $Cs_2O$ | 1-30 |
| $SnO_2$ | >4-15 |
| F | ≥0.5 |
| $BaO + Cs_2O + SnO_2 + F$ | ≥10. |

2. The radiopaque glass as defined in claim 1, wherein said composition comprises not more than 5 wt. % of F.

3. The radiopaque glass as defined in claim 1, wherein said composition comprises, in wt. % on an oxide basis:

| | |
|---|---|
| $SiO_2$ | 38-70 |
| $B_2O_3$ | 6-15 |
| $Al_2O_3$ | 1-7 |
| $K_2O$ | 0-7 |
| BaO | 0.8-20 |
| $Cs_2O$ | 1-28 |
| $SnO_2$ | >4-15 |
| F | 0.75-2.5 |
| $BaO + Cs_2O + SnO_2 + F$ | ≥10. |

4. The radiopaque glass as defined in claim 1, wherein the sum of $BaO+Cs_2O+SnO_2+F$ is ≥12 wt. %.

5. The radiopaque glass as defined in claim 1, wherein a molar ratio of $SnO_2$ to F is at least 0.4.

6. The radiopaque glass as defined in claim 1, wherein a molar ratio of $SnO_2$ to F is at most 0.85.

7. The radiopaque glass as defined in claim 1, wherein a molar ratio of $Cs_2O$ to the sum of $BaO+Cs_2O+SnO_2$ is at least 0.05.

8. The radiopaque glass as defined in claim 1, wherein a molar ratio of $Cs_2O$ to the sum of $BaO+Cs_2O+SnO_2$ is at most 0.48.

9. The radiopaque glass as defined in claim 1, further comprising at least one of the following components in the amount in wt. % based on oxide content as follows:

| | |
|---|---|
| $ZrO_2$ | 0-2 |
| ZnO | 0-2 |
| MgO | 0-2 |
| CaO | 0-2 |
| $WO_3$ | 0-2 |
| $Nb_2O_5$ | 0-2 |
| $HfO_2$ | 0-2 |
| $Ta_2O_5$ | 0-2 |
| $Gd_2O_3$ | 0-2 |
| $Sc_2O_3$ | 0-2 |
| $Y_2O_3$ | 0-2 |
| $Yb_2O_3$ | 0-2 |
| $La_2O_3$ | 0-2. |

10. The radiopaque glass as defined in claim 1, which is, apart from at most impurities, free of at least one of $Na_2O$, $Li_2O$, MgO, $CeO_2$, $TiO_2$, $La_2O_3$ and $ZrO_2$.

11. The radiopaque glass as defined in claim 1, which has a refractive index $n_d$ in the refractive index range between 1.48 and 1.56 and a relative aluminum equivalent thickness ALET (%) greater than or equal to a minimum value according to the following equation (I):

$$\text{Min. relative ALET}(\%) = C*n_d - D, \text{ wherein } C=11000 \text{ and } D=16160.$$

12. The radiopaque glass as defined in claim 11, which has a refractive index $n_d$ in the refractive index range between 1.48 and 1.56 and a relative aluminum equivalent thickness ALET (%) smaller than or equal to a maximum value according to the following equation (II):

$$\text{max. relative ALET}(\%) = A*n_d - B, \text{ wherein } A=11430 \text{ and } B=16230.$$

13. The radiopaque glass as defined in claim 1, which has a minimum relative ALET of 120% and a maximum relative ALET of 700% when $n_d$ is from 1.48 to <1.49; a minimum relative ALET of 260% and a maximum relative ALET of 1000% when $n_d$ is from 1.49 to <1.51; a minimum relative ALET of 520% and a maximum relative ALET of 1200% when $n_d$ is from 1.51 to <1.53; a minimum relative ALET of 780% and a maximum relative ALET of 1500% when $n_d$ is from 1.53 to <1.55; and a minimum relative ALET of 850%, and a maximum relative ALET of 1600% when $n_d$ is from 1.55 to 1.56.

14. The radiopaque glass as defined in claim 1, which has a minimum relative ALET of 120% and a maximum relative ALET of 760% when $n_d$ is from 1.48 to <1.49; a minimum relative ALET of 240% and a maximum relative ALET of 875% when $n_d$ is from 1.49 to <1.50; a minimum relative ALET of 360% and a maximum relative ALET of 990% when $n_d$ is from 1.50 to <1.51; a minimum relative ALET of 475% and a maximum relative ALET of 1105% when $n_d$ is from 1.51 to <1.52; a minimum relative ALET of 590% and a maximum relative ALET of 1220% when $n_d$ is from 1.52 to <1.53, a minimum relative ALET of 705% and a maximum relative ALET of 1335% when $n_d$ is from 1.53 to <1.54; a minimum relative ALET of 820% and a maximum relative ALET of 1450% when $n_d$ is from 1.54 to <1.55; and a minimum relative ALET of 935% and a maximum relative ALET of 1565% when $n_d$ is from 1.55 to 1.56.

15. The radiopaque glass as defined in claim 1, in which 95 wt. % has a composition consisting, in wt. % on an oxide basis, of:

| | |
|---|---|
| $SiO_2$ | 35-75 |
| $B_2O_3$ | 5-15 |
| $Al_2O_3$ | 0.8-7.5 |

-continued

| | |
|---|---|
| K$_2$O | 0-10 |
| BaO | 0.6-24 |
| Cs$_2$O | 1-30 |
| SnO$_2$ | >4-15 |
| F | ≥0.5 |
| BaO + Cs$_2$O + SnO$_2$ + F | ≥10. |

16. A glass for diagnostic purposes in humans or animals, said radioactive glass having a refractive index n$_d$ of 1.48 to 1.56, which is free of PbO apart from at most impurities, said radioactive glass having a composition comprising, in wt. % on an oxide basis

| | |
|---|---|
| SiO$_2$ | 35-75 |
| B$_2$O$_3$ | 5-15 |
| Al$_2$O$_3$ | 0.8-7.5 |
| K$_2$O | 0-10 |
| BaO | 0.6-24 |
| Cs$_2$O | 1-30 |
| SnO$_2$ | >4-15 |
| F | ≥0.5 |
| BaO + Cs$_2$O + SnO$_2$ + F | ≥10. |

17. A dental glass for treating cavities in teeth, or for a dental restoration, in humans or animals, said dental glass comprising a radiopaque glass having a refractive index n$_d$ of 1.48 to 1.56, which is free of PbO apart from at most impurities, said radiopaque glass having a composition comprising, in wt. % on an oxide basis

| | |
|---|---|
| SiO$_2$ | 35-75 |
| B$_2$O$_3$ | 5-15 |
| Al$_2$O$_3$ | 0.8-7.5 |
| K$_2$O | 0-10 |
| BaO | 0.6-24 |
| Cs$_2$O | 1-30 |
| SnO$_2$ | >4-15 |
| F | ≥0.5 |
| BaO + Cs$_2$O + SnO$_2$ + F | ≥10. |

18. The dental glass as defined in claim 17, in the form of a powder or particulate consisting of particles.

19. The dental glass as defined in claim 17, consisting of powder particles with surfaces that are silanized.

20. A polymer-based dental composition comprising a dental polymer and a dental glass as defined in claim 17.

21. A dental cement comprising a dental glass as defined in claim 17.

22. The dental cement as defined in claim 21, wherein it is a polymer-reinforced glass ionomer cement containing the dental glass, wherein the dental glass is in the form of an inert additive.

23. A cover or substrate glass for display technology or photovoltaics, said cover or said substrate glass comprising a lead-free radiopaque glass as defined in claim 1.

24. An embedding material for a radioactive material comprising a lead-free radiopaque glass as defined in claim 1.

25. An X-ray or cathode ray tube comprising a lead-free radiopaque glass as defined in claim 1.

26. An element for optical applications, comprising a lead-free radiopaque glass as defined in claim 1.

* * * * *